United States Patent [19]

Blasetti

[11] 4,061,019
[45] Dec. 6, 1977

[54] APPARATUS FOR GENERATING FORCES IN A SPECIMEN

[76] Inventor: David H. Blasetti, 7019 Guilford Road, Philadelphia, Pa. 19082

[21] Appl. No.: 667,450

[22] Filed: Mar. 16, 1976

[51] Int. Cl.² .............................................. B06B 1/10
[52] U.S. Cl. ...................................... 73/662; 233/25
[58] Field of Search ............... 73/67, 67.2, 67.3, 67.4, 73/71.5 R, 71.6; 233/25

[56] References Cited
U.S. PATENT DOCUMENTS 2,301,967   11/1942   Nosker et al. ..................... 73/71.5 X
2,822,127   2/1958    Sinn .................................... 233/25 X

FOREIGN PATENT DOCUMENTS 178,780   6/1954   Austria .................................. 233/25

Primary Examiner—Richard C. Queisser
Assistant Examiner—John P. Beauchamp
Attorney, Agent, or Firm—Dorfman, Herrell and Skillman

[57] ABSTRACT

Apparatus for creating vibratory forces in a specimen in which the specimen is positioned within a carrier which is rotated about a remote axis, preferably vertical, to generate centrifugal forces directed radially outward from the remote axis. The carrier is also rotated about an axis perpendicular to the direction of the radial centrifugal force so that the force on any particle is cyclically reversed at a frequency determined by the frequency of the rotation about the perpendicular axis. The rate of rotation about the remote axis may be varied to vary the amplitude of the centrifugal force and the rate of rotation about the perpendicular axis may be varied to vary the frequency of the vibratory force generated by this combination. The specification discloses an apparatus in which a solid specimen may be mounted for the generation of cyclically-varying vibration forces and also an apparatus for receiving a liquid which may be subjected to cyclically-varying vibrational forces.

9 Claims, 4 Drawing Figures

APPARATUS FOR GENERATING FORCES IN A SPECIMEN

The present invention relates to apparatus for generating vibratory forces in a specimen and is particularly applicable to a mechanism which combines predetermined rotary motions to produce controlled reciprocatory impulses for the purpose of testing the effect of vibratory forces upon the specimen.

Prior to the present invention, there has been no satisfactory method for subjecting specimens to accurately controlled vibratory forces of substantial magnitude. The usual vibration-inducing apparatus comprises a resilient mounting device which is subjected to vibratory forces which displace the tested specimen at a predetermined frequency and rely upon the resilient recovery of the mounting structure to generate the vibratory forces applied to the specimen. Although somewhat satisfactory for vibrations of low magnitude and of limited frequency, such apparatus is not conducive to producing vibratory forces of large magnitude over a wide range of frequencies.

With the foregoing in mind, the present invention provides apparatus which utilizes the radial force generated by rotational movement about a remote first axis at a controlled angular velocity in combination with a controlled rotation of the specimen about a second axis perpendicular to the direction of the radial force so as to generate within the specimen a vibratory force having a magnitude determined by the radius and angular velocity of the first-mentioned rotational movement and a frequency determined by the rate of rotary movement of the second-mentioned rotation.

Specifically, the present invention provides a vibration testing device having means for rotating the specimen about a remote axis at a predetermined velocity and a predetermined radial distance from the axis so as to generate a predetermined radial force along with means to rotate the specimen about an axis perpendicular to the radial direction at a predetermined frequency of rotaton so that the radial force generated at any individual point within the body of the specimen by the first-mentioned rotation is directed alternately toward and away from the axis of the second rotation as the specimen rotates about the latter axis.

The present invention provides a mechanism for generating a plurality of differential forces within a body, which, when combined or integrated, counteract one another so as to minimize the eccentric loading necessary to generate the forces.

The invention has primary utility in vibration testing, but is also applicable in other disciplines which may utilize the application of acceleration forces within a body.

The objects of the invention are more fully set forth hereinafter with reference to the accompanying drawing, wherein.

Figure 1:
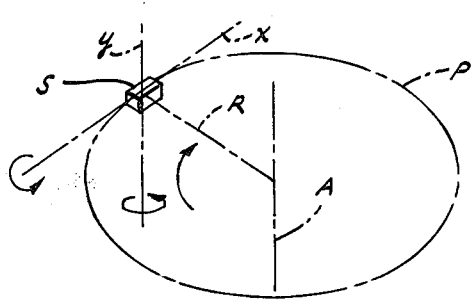
FIG. 1 is a diagram illustrating the mode of operation obtained by the present invention.

The generation of force in the test specimen is illustrated in FIG. 1. In FIG. 1, the specimen is indicated by the reference character S. The specimen is rotated about a remote central axis A, in the present instance, a vertical axis spaced from the specimen by a radial length R. As the specimen S rotates about the axis at the distance R, a centrifugal force is generated resulting from the acceleration from the body as it travels in a circular path, for example the path indicated at P in FIG. 1. When the specimen rotates at a constant speed, for example an angular velocity of $\omega$, the acceleration forces generated in a radial direction are directly proportional to the square of the angular velocity ($\omega^2$) times the radius R, or stated differently, to the square of the tangential velocity ($v^2$) over R. The radial force generated by the rotation of the specimen about the axis A is directed outwardly. The total force applied to the body by rotation about the axis A is the integrated sum of the forces applied to each point within the body. The force applied at any point within the body is a differential force proportional to $v^2/R$ in an outward direction. Since it is desired to impart a vibratory stress upon the specimen, the specimen is rotated about an axis perpendicular to the radial force along the radius R. As shown in FIG. 1, the body may be rotated about a horizontal axis $x$ tangential to the path P, about a vertical axis $y$ perpendicular to the path P or at any angle within the plane defined by the axes $x$ and $y$. Rotating the specimen S about a perpendicular axis, for example the $x$ axis, at an angular rate of $n$ revolutions per second causes the direction of the force applied to a particular in the specimen S to be reversed wice for each revolution, so that the speed of revolution of the specimen S about the secondary axis $x$ determines the frequency of the vibratory force generated in the specimen. The force generated by rotation about the secondary axis may be disregarded where the angular velocity about the secondary axis is small. In other words, as the specimen S rotates about the axis $x$, the centrifugal force generated by the rotation about th axis A varies cyclically between a maximum force directed away from the $x$ axis to a maximum force directed toward the $x$ axis as each point within the specimen rotates about the $x$ axis. The same cyclic variation of the direction of application of the centrifugal force occurs regardless of the orientation of the secondary axis within the plane defined by the $x$ and $y$ axis, and regardless of the position of the secondary axis relative to the center of gravity of the specimen.

It should be noted that the force generated by the rotation of the specimen about the axis A is a constant centrifugal force which results from driving the specimen about the circular path P. However, by reason of the specimen being rotated about a secondary axis $x$ during the rotation about the axis A, the constant centrifugal force is cyclically varied in direction to produce a vibrational force upon each particle within the specimen S.

Figure 2:
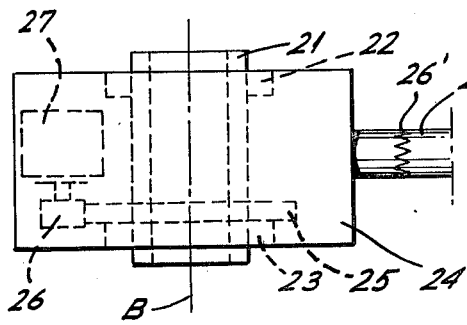
FIG. 2 is a diagrammatic view illustrating a structure embodying the present invention for testing a work specimen which may be clamped in place therein.

FIG. 2 illustrates a suitable apparatus for manipulating the specimen in accordance with the diagram shown in FIG. 1. In FIG. 2, the specimen is operable to be clamped within a carrier or mounting tube 21 which is rotatably mounted, for example by bearings 22 and 23, in a carriage 24. The mounting tube 21 has a gear wheel 25 fixed thereto, and the gear wheel meshes with a drive pinion 26 carried by the shaft of a drive motor 27 mounted on the carriage 24. Thus, the drive motor 27 operates to rotate the sleeve 21 about the central axis of the sleeve, as indicated at $y$ in FIG. 2. The carriage 24 is mounted at the remote end of an arm 24a having a splined joint at 26' which permits the carriage to be rotated about the axis of the arm 24a so as to position the axis B at any desired perpendicular orientation to the axis of the arm 24a. Referring to the diagram of FIG. 1, the axis B may coincide with axis x, the axis y, or any axis within the plane defined by the axes x and y. Preferably, the specimen is mounted in the tube 21 so that its center of gravity lies on the axis B, so as to minimize the power needed to rotate the specimen and to avoid the adverse effects of unbalanced forces.

The arm 24a is constructed to rotate about a central support shaft 31 which defines the central axis of rotation for the structure, such as the axis A shown in FIG. 1. The arm 24a terminates at its inner end in a bearing block 32 which mounts the bearings for mounting the rod on the shaft 31. The bearing block 32 includes an extending sleeve 33 having bearings therein and a drive gear 34. In addition, the sleeve 33 carries a pair of slip rings 35 and 36 which provide electrical connections to the motor 27 for providing the driving force for roatating the motor 27. Suitable brushes cooperate with the slip rings 35 and 36 and are mounted within a housing 37 having an electrical input at 38.

The sleeve 33 an the arm 24a are rotated about the axis by a drive worm 39 mounted in engagement with the drive gear 34 and operable to rotate, for example by a motor 40, the arm 24a at a suitable angular speed to obtain the desired centrifugal force to which the specimen is subjected. Thus, in the structure shown in FIG. 2, the magnitude of the vibratory force is controlled by controlling the speed of rotation imparted by the drive means 40 through the worm 39. The magnitude of the force is proportional to the square of the angular velocity and is inversely proportional to the length of the arm 24a, as indicated at R in FIG. 1. Since the arm 24a is preferably of fixed length, the only variable required for changing the magnitude of the force applied to the specimen S within the sleeve 21 is the angular speed about the remote axis A imparted by the drive means 40. The frequency of the vibration is controlled by the rotary speed of the motor 27 which is directly controlled by the input through the slip rings 35 and 36. By controlling the input applied to the motor, the speed of rotation may be increased to thereby increase the frequency of the vibratory forces generated in the specimen within the tube 21. To limit the eccentric loading, the bearing block is counterbalanced to the weight of the arm 24a, the carriage 24 and the specimen in the carrier 21.

The structure of FIG. 2 is reduced to a simple form and it is apparent that different structures may be employed for producing the desired vibratory forces. In the structure of FIG. 2, the carriage 24 is mounted at the remote end of an arm, but it is within the skill of a designer to provide a carriage on a suitable rotary track which may be driven about the track at a constant speed to produce a centrifugal force in a specimen carried by the carriage about the circular path corresponding to the path P of FIG. 1. The carriage may include a carrier device for rotating the specimen about an axis perpendicular to the radial force generated by the travel of the carriage in the circular path. The equipment may be designed to impart forces ranging from a fraction of to multiples of the gravitational forces without difficulty and the frequency of the cyclic variation of the force may be varied within wide limits, depending only upon the rotation of the specimen about its secondary axis.

Figure 3:
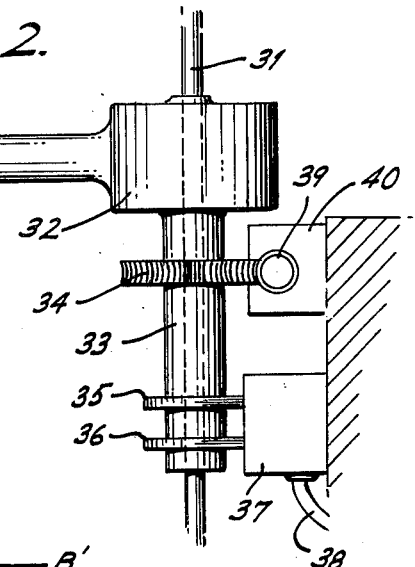
FIG. 3 is a view illustrating a mechanism embodying the present invention for testing a specimen in liquid form.
Figure 3:
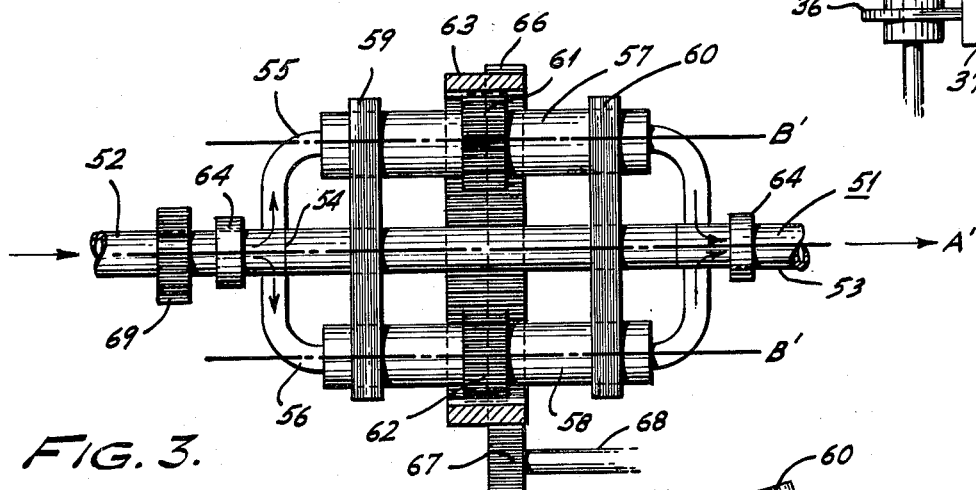
Figure 4:
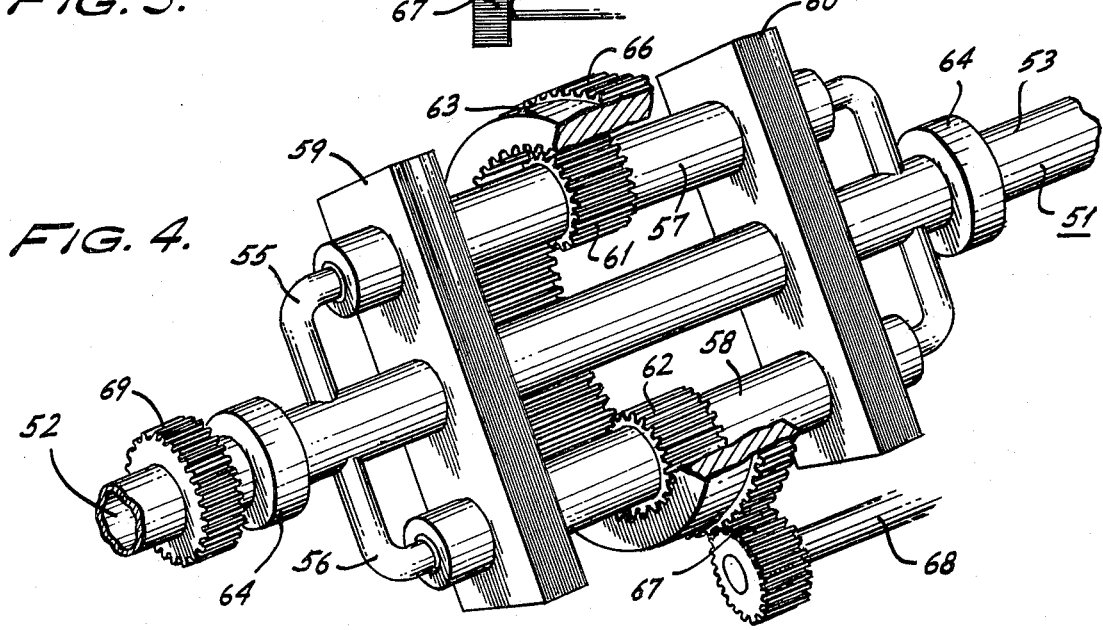
FIG. 4 is a perspective view of the structure shown in FIG. 3.

The preceding discussion has been directed towards the testing of solid structures which are rigidly mounted in the test apparatus. However, the invention is equally applicable to applying vibratory forces upon fluids and materials carried in a fluid stream. FIGS. 3 and 4 illustrate a suitable apparatus for imparting cyclically-varying forces to a fluid. In the present instance, the apparatus is designed to accommodate a fluid which is flowing through the apparatus as indicated by the arrows in FIG. 3, but it is also applicable to a batch of fluid which may be introduced into the apparatus as indicated by the first arrow and subjected to the test forces and then withdrawn from the apparatus as indicated by the second arrow.

FIG. 3 illustrates apparatus comprising a hollow main shaft 51 which, in the present instance, is connected to a liquid supply at its lefthand end, as indicated at 52 and to a liquid discharge at 53. Between the supply and discharge ends 52 and 53, the shaft is plugged, as indicated at 54, so as to divert the liquid into branch conduits 55 and 56, extending outwardly respectively from opposite sides of the shaft 51. The branch conduits 55 and 56 lead into multiple elongated carriers or treatment chambers 57 and 58 which are disposed parallel to the main shaft 51 and are spaced radially therefrom, for example by mounting structures 59 and 60.

Each of the chambers 57 and 58 is rotatable within the structures 59 and 60 and has a planet gear 61 or 62, respectively, fixed thereon to drive the chambers about their individual axes. The planet gears 61 and 62 mesh with a ring sun gear 63 so that as the shaft 51 is rotated about its axis A', for example, on bearings 64 adjacent the ends 52 and 53, the individual chambers 57 and 58 may be rotated about their axes B'. In the present instance, the ring gear 63 has external drive teeth 66 thereon which mesh with an external drive pinion 67 having a drive shaft 68 therefor. Thus, the rotation of the ring gear 63 may be controlled by the drive shaft 68 to either maintain the gear stationary or to drive it for concurrent or countercurrent rotation with the shaft 51. The rotation of the ring gear 63 controls the rotation of the chambers 57 and 58 about their respective axes B'. The shaft 51 is driven by a suitable gear 69 to cause the chambers 57 and 58 to rotate about the central axis A'. Thus, the apparatus of FIG. 3 operates to displace the liquid within the chambers 57 and 58 in a manner similar to the displacement of the specimen S in FIG. 1, the axis A' in FIG. 3 corresponding to the axis A in FIG. 1, and the axis B' in FIG. 3 corresponding to the axis y in FIG. 1. Thus, the liquid, and any particle entrained therein, within either of the chambers 57 and 58 is subjected to cyclic forces determined by the angular rotation of the shaft 51 about its axis and at a frequency determined by the rotation of the chambers 57 and 58 about their respective axes B'.

The utility of the structure shown in FIGS. 3 and 4 is not limited to the testing of materials in liquid form for vibratory forces, but has utility in subjecting liquids to forces which will mix homogeneously. The cyclically-varying forces applied to the liquid are effective to provide a thorough mixing of the liquid passing through the chambers 57 and 58. As with the mechanical device, the magnitude of the force applied is proportional to the angular rotation of the device around the axis A' and the radial distance between the axes A' and B', and the cyclic frequency of the force is determined by the revolutionary speed of the chambers 57 and 58 about their respective axes.

Thus, in both of the illustrated embodiments, the specimen is subjected to cyclically-varying forces while in a carrier. The carrier is rotated about a first axis at a speed to generate a centrifugal force of a specified magnitude on each particle of the specimen, and the carrier is rotated about a second axis perpendicular to the direction of the centrifugal force to effect cyclic variation of the orientation of the centrifugal force generated on each particle.

While particular embodiments of the present invention have been herein illustrated and described, it is not intended to limit the invention to such disclosures but changes and modifications may be made therein and thereto within the scope of the following claims. For example, the embodiment of FIG. 2 includes an electric motor 27 driven by electrical connections extending through the arm 25 to the slip rings 35 and 36 which serve as a power take-off. Alternatively, the motor may be battery-driven or another mechanism having its own power source may be provided to rotate the specimen. Other variations will be apparent to those skilled in the art.

I claim:

1. Apparatus for generating cyclically-varying forces in a solid specimen comprising a carrier for the specimen, mounting means in said carrier to fix said specimen in said carrier, means to rotate the carrier about a remote first axis at a given angular speed, whereby a centrifugal force radial to said first axis is generated by each particle in the specimen, means for effecting rotation of said specimen about a second axis perpendicular to the direction of the radial centrifugal force to thereby cyclically reverse the orientation of the centrifugal force generated by each particle in the specimen.

2. Apparatus according to claim 1 wherein said means to rotate the carrier comprises a carriage and means to cause said carriage to travel in a circular path about said first axis, said carriage having means mounting said carrier for rotation thereon about said second axis, and drive means on said carriage for effecting said rotation of said carrier and thereby rotation of the specimen fixed therein on said second axis.

3. Apparatus according to claim 2, including a central support shaft coaxial with said first axis, a support bearing rotatable on said shaft, means to rotate said bearing on said shaft, and a radial arm carried by said bearing mounting said carriage at its outer end whereby upon rotation of said support bearing said carriage moves said carrier in said circular path.

4. Apparatus according to claim 3, including means on said arm to adjust the angular orientation of said carriage on said shaft so as to adjust the orientation of said second axis relative to said first axis angularly about said radial arm.

5. Apparatus according to claim 2 wherein said mounting means in said carrier comprises a tubular sleeve having an axial bore receiving said specimen, said carriage drive means rotating said carrier about the axis of said bore.

6. A method of testing a solid-body specimen by subjecting the specimen to a vibratory force comprising the steps of rotating said specimen about a remote first axis at a given speed, whereby a centrifugal force radial to said first axis is generated by each particle in th specimen, and simultaneously effecting rotation of said specimen about a second axis perpendicular to the direction of the radial centrifugal force to thereby cyclically reverse the orientation of the centrifugal force generated by each particle in the specimen.

7. A method according to claim 6 wherein said specimen is tested by fixing said specimen in a carrier, and causing said carrier to travel in a circular path of a given radius about said first axis at a predetermined velocity, and rotating said carrier about said second axis at a predetermined velocity.

8. A method according to claim 6 wherein the magnitude of the centrifugal force is determined by regulating the speed of rotation about said first axis and the remoteness of the first axis, and the cycle of the reversal is determined by regulating the frequency of the rotation of said specimen on said second axis.

9. A method according to claim 8 wherein said specimen has a center of gravity coincident with said second axis.

* * * * *

UNITED STATES PATENT OFFICE
CERTIFICATE OF CORRECTION

Patent No. 4,061,019  Dated December 6, 1977

Inventor(s) David H. Blasetti

It is certified that error appears in the above-identified patent and that said Letters Patent are hereby corrected as shown below:

[76] "Philadelphia, Pa." should be --Upper Darby, Pa.--;
Column 1, line 42, "rotaton" should be --rotation--;
Column 2, line 31, "particular" should be --particle--;
Column 2, line 32, "wice" should be --twice--;
Column 2, line 40, "th" should be --the--;
Column 3, line 21, "roatat-" should be --rotat- --;
Column 3, line 25, "an" should be --and--;
Claim 6, line 5,   "th" should be --the--.

Signed and Sealed this

Seventh Day of March 1978

[SEAL]

Attest:

RUTH C. MASON
Attesting Officer

LUTRELLE F. PARKER
Acting Commissioner of Patents and Trademarks